United States Patent [19]
Aleles et al.

[11] Patent Number: 6,068,847
[45] Date of Patent: May 30, 2000

[54] COSMETIC COMPOSITIONS

[75] Inventors: Margaret Aleles, Gladstone; Claudia Kaminski, Milford, both of N.J.; Curtis A. Cole, Langhorne, Pa.

[73] Assignee: Johnson & Johnson Consumer Products, Inc., Skillman, N.J.

[21] Appl. No.: 08/940,880

[22] Filed: Sep. 30, 1997

Related U.S. Application Data

[60] Provisional application No. 60/027,552, Oct. 3, 1996.

[51] Int. Cl.⁷ ........................................................ A61K 7/48
[52] U.S. Cl. .......................... 424/401; 424/450; 514/725; 514/844; 514/846; 514/937
[58] Field of Search ...................................... 424/401, 450; 514/937, 725, 844, 846

[56] References Cited

U.S. PATENT DOCUMENTS

| | | | |
|---|---|---|---|
| 3,906,108 | 9/1975 | Felty | 424/318 |
| 5,693,330 | 12/1997 | Granger et al. | 424/401 |

FOREIGN PATENT DOCUMENTS

| | | |
|---|---|---|
| 0 094 771 | 11/1983 | European Pat. Off. . |
| 0 631 772 A2 | 4/1995 | European Pat. Off. . |
| WO 96/31194 | 10/1996 | WIPO . |
| WO 97/31620 | 4/1997 | WIPO . |

*Primary Examiner*—Jyothsna Venkat
*Attorney, Agent, or Firm*—Andrea L. Colby

[57] ABSTRACT

This invention relates to low-irritation profile compositions for skin care containing retinoids.

1 Claim, No Drawings

COSMETIC COMPOSITIONS

This application claims the benefit of Provisional Application No. 60/027,552 filed on Oct. 3, 1996.

FIELD OF THE INVENTION

This invention relates to skin care compositions containing retinoids which generally improve the quality of the skin, particularly human facial skin. More particularly, the present invention relates to chemically stable skin care compositions comprising an emulsion or in the form of a liposomal, system, which have low irritation profiles. This invention also relates to said compositions containing certain retinoids and to methods of making such compositions.

BACKGROUND OF THE INVENTION

Skin care compositions containing retinoids have become the focus of great interest in recent years. Retinoic acid, also known as Vitamin A acid or tretinoin, is well-known for the treatment of such skin conditions as acne and products containing retinoic acid are commercially available in various forms from the Dermatological Division of Ortho Pharmaceutical Corporation. Such products, for example, include Retin A* creams, an oil-in-water emulsion of retinoic acid containing as an oil-soluble antioxidant, butylated hydroxytoluene (BHT); Retin A* liquid, a solution of retinoic acid in a polyethylene glycol/ethanol solvent employing BHT as an antioxidant; and Retin A* gel, which comprises retinoic acid in a gel vehicle comprising ethyl alcohol as the solvent, hydroxypropyl cellulose as the thickener or gelling agent and BHT as an antioxidant. These retinoic acid containing products have proven stable and capable of providing active ingredients after extended periods of storage.

More recently, however, wide use of retinoids has been suggested for treatments other than acne such as, for example, the treatment of skin against photoaging and sun damage. Many individuals who have had a good deal of sun exposure in childhood will show the following gross cutaneous alterations in later adult life: wrinkling, leatheriness, yellowing, looseness, roughness, dryness, mottling (hyperpigmentation) and various premalignant growths (often subclinical). These changes are more prominent in light-skinned persons who burn easily and tan poorly. These cumulative effects of sunlight are often referred to as "photoaging". Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

The problem of skin aging is addressed in U.S. Pat. No. 4,603,146 wherein Vitamin A acid in an emollient vehicle is suggested as a treatment. Further, in U.S. Pat. No. 4,877,805, it is suggested that a number of retinoids are useful for restoring and reversing sun damage of human skin.

When considering the use of retinoids in skin care products, it is believed that certain retinoids such as, for example, retinol (Vitamin A alcohol), retinal (Vitamin A aldehyde) and retinyl esters such as retinyl acetate and retinyl palmitate would be preferred over retinoic acid. A preferred form is retinol. This is because retinol is an endogenous compound naturally occurring in the human body and essential for good growth, differentiation of epithelial tissues and reproduction. Retinol is also preferred because it has a much larger safety margin than other retinoids such as retinoic acid. Additionally, excess retinol is stored in the human body largely in an inactive ester form, e.g. retinyl palmitate and, to some extent, retinyl acetate. The aldehyde, retinal, also a preferred form, is an active metabolite of retinol and is needed for visual function. Accordingly, attention has turned toward formulating skin care compositions which contain these preferred, naturally occurring retinoids.

In formulating products containing such retinoids, the same properties sought with respect to the retinoic acid formulas are desirable for other retinoid containing compositions. Specifically, much attention is directed toward providing a composition which is aesthetically pleasing and which can deliver active ingredients after a substantial shelf life. Not surprising, in formulating products containing such retinoids, the art is led to the experience gained in the already existing formulas containing retinoic acid. Typically, such formulas comprise oil-in-water emulsions wherein the retinoic acid is carried within the oil phase and is protected from oxidation by employing an oil-soluble antioxidant. With respect tot he form of the emulsion, oil-in-water emulsions have been preferred in that, as compared to water-in-oil emulsions for example, they are non-occlusive, non-greasy, compatible with other such emulsion products, easy to remove from the skin and are regarded as more aesthetically pleasing as well as being more economical to manufacture. With respect to chemical stability of the active ingredient, it has been experienced that the retinoic acid in the oil phase is, in the main, well protected by including in such oil phase an oil soluble antioxidant.

Thus, for example, the aforementioned Retin A* cream is an oil-in-water emulsion containing retinoic acid and BHT, an oil-soluble antioxidant. In U.S. Pat. No. 3,906,108 there is disclosed an oil-in-water emulsion of retinoic acid which may include an oil-soluble antioxidant such as BHT or dl-a-tocopherol and a chelating agent e.g. ethylenediaminetetraacetic acid (EDTA). In U.S. Pat. No. 4,466,805, a tanning composition is described which may include, among other ingredients, Vitamin A in an oil-in-water emulsion containing Vitamin E and citric acid. In U.S. Pat. No. 4,247,547 still another form of a retinoic acid containing composition, namely a gel, is disclosed and is protected by an antioxidant selected form the group consisting of butylated hydroxytoluene, butylated hydroxyanisole (BHA), ascorbic acid (Vitamin C), propyl gallate, and a-tocopherol (Vitamin E).

In U.S. Pat. No. 4,826,828 it is suggested that a stable composition comprising retinol, retinyl acetate and retinyl palmitate may consist of retinol in a water-in-oil emulsion wherein the emulsion further include two oil-soluble antioxidants, BHT and BHA.

Further, Avon Products, Inc., the assignee of U.S. Pat. No. 4,826,828, sells two skin care products called Bioadvance and Bioadvance 2000. Each of these products is supplied in two bottles, portions of which are mixed together just prior to use. The first bottle contains what is called "skin lotion", while the second bottle contains what is called a "fortifier". The "skin lotion" is a water-in-oil emulsion having a number of ingredients which include water, emulsifiers, silicone and vegetable oils, preservatives, emollients and butylated hydroxytoluene (BHT). The "fortifier" is a solution which contains a number of ingredients including cyclomethicone (a silicone oil), denatured ethanol, an emulsifier (Polysorbate 20), retinol, retinyl acetate, retinyl palmitate, BHT and BHA. When a specified portion of the "fortifier" is added to a specified portion of the "skin lotion" and mixed, there results a water-in-oil emulsion which comprises retinol, retinyl acetate, retinyl palmitate, BHT and BHA, the latter being oil-soluble antioxidants. The outer package in which Bioadvance is supplied carries a statement which says "Because BIOADVANCE begins to lose effectiveness after one month, for maximum benefits, use a fresh supply each month". It would appear from this statement that the chemical stability of the retinoids in the mixture of the "skin lotion" and the fortifier" is quite limited. The fact that in both the BIOADVANCE and BIOADVANCE 2000 products the "fortifier" ingredients must be mixed with the "skin lotion" ingredients immediately prior to use indicates that the resulting water-in-oil emulsion which is applied to the skin also has limited chemical stability of one or more of the above-mentioned retinol, retinyl acetate and retinyl palmitate.

Further still, U.S. Pat. No. 4,720,353 to Bell discloses water-in-oil emulsion carriers for various medicaments and drugs intended for topical application to the skin. Water soluble, miscible or dispersible drugs may be incorporated into the aqueous phase of the emulsion. Oil-soluble, miscible or dispersible drugs may be incorporated into the oil phase. Drugs which may be incorporated into the emulsion include derivatives of retinoic acid. Ingredients which may optionally be added to the emulsion include a preservative such as methyl paraben, propyl paraben or imidazolidinyl urea or an antioxidant such as butylated hydroxyanisole and a water or oil soluble vitamin such as vitamin C, tocopherol linoleate and the like.

Still further, EP 0 343 444 A2 to Siemer et al. discloses cosmetic preparations based on retinyl palmitate. Example 3 discloses a night cream in the form of an water-in-oil type emulsion comprising retinyl palmitate and butylated hydroxyanisole (BHA). Example 4 describes a water-in-oil emulsion comprising retinyl acetate and a-tocopherol (Vitamin E).

Still further, EP 0 330 496 A2 to Batt is directed to skin treatment compositions comprising a topically acceptable base and an effective amount of at least one ester of retinol, said compositions being useful in the treatment of photoaged skin. Example 6 describes a water-in-oil emulsion comprising Vitamin A propionate and BHT, an oil-soluble antioxidant.

U.S. Pat. Nos. 5,559,149 and 5.652,263 (Wang et al.), describe water-in-oil emulsions which provide a stable retinol formulation. U.S. Ser. Nos. 08/523,836, 08/609,588, and 08/807,351 describe oil-in-water emulsions which provide a stable retinol formulation. U.S. Ser. No. 08/902,922 describes liposome-containing formulations which provide stable retinol formulations.

The topical application of retinoid-containing compositions is well-known to result in beneficial skin changes. Retinoids effect treatment for acne and skin damage due to exposure to sunlight. However, the topical application of retinoids can cause significant irritation characterized by erythema, redness, scaling, edema or itching. Many attempts have been made to reduce irritation associated with the application of retinoids to the skin.

For example, U.S. Pat. No. 5,470,567 describes a composition containing retinoids and 4-hydroxyanisole which does not contain corticosteroids yet exhibits diminished irritation. Similarly, U.S. Pat. No. 4,727,088 describes an emulsified formulation which contains fatty alcohols and results in reduced irritation.

U.S. Pat. No. 5,061,692 describes reducing irritation by topically applying specific penta-peptides or their salts to the skin in addition to the retinoid compositions.

Other methods of reducing retinoid-induced irritation have been suggested. For example, U.S. Pat. No. 5,075,340 describes the use of certain derivatives of retinoic acid in the compositions, such as retinoic acid glucuronide, to avoid skin irritation.

Irritation due to retinoids has also been mitigated through the use of different types of delivery systems.

European Patent application No. EP 472225 describes a pharmaceutical composition based on hydrated lamellar phases or liposomes which contain retinoic acid as the active material, which is said to reduce the irritation while maintaining activity or efficacy.

U.S. Pat. No. 4,911,928 describes another type of lipid vesicle, the paucilamellar vesicles (PLV) which have a capacity of transporting a greater amount of lipophilic material. A subsequent patent, U.S. Pat. No. 5,147,723, describes non-phospholipid surfactants which can form paucilamellar vesicles.

None of the previous suggestions has proven to be low in irritation, as the retinoids contained in these products are quite potent and very irritating. It is therefore, desirable to develop skin care products containing retinoids which are not only efficacious and cosmetically elegant, but substantially free of harsh irritating side effects which discourage continued use of retinoids for treatment of skin conditions.

It is another object of this invention to provide skin care compositions containing retinoids which have little or no irritancy and which do not necessitate special ingredients or manufacturing, storage, handling precautions.

SUMMARY OF THE INVENTION

It has now been discovered that, unexpectedly, retinoid-containing compositions may be formulated that exhibit good efficacy, cosmetic elegance but which induce only very low irritation.

The compositions of this invention contain (a) a retinoid compound, such as retinoic acid, retinol, retinaldehyde and/or various other known related retinoid compounds including esters of retinoic acid and the like; (b) an oil-soluble antioxidant; and (c) emulsifiers or surfactants in a pharmaceutically and cosmetically acceptable vehicle in which the combination of components is particularly non-irritating together with said retinoid compound. Similar retinoid-containing compositions may be found in co-pending U.S. patent application Ser. No. 08/415,975, which is hereby incorporated herein by reference.

The compositions of this invention are preferably emulsions, the emulsions preferably containing an oil phase having ingredients which may be made into paucilamellar vescicle, although it has been found that such vescicles need not be formed in order to achieve a low-irritation product. As described above, the composition of the invention is in the form of a particular type of emulsion, namely oil-in-water. As used herein, the generally accepted concept of an emulsion applies, i.e., an intimate mixture of two immiscible liquids which remains unseparated for an acceptable shelf life at or about room temperature. Ordinarily, when two immiscible liquids are mechanically agitated, both phases initially tend to form droplets. Thereafter, when the agitation ceases, the droplets quickly coalesce, and the two liquids tend to separate.

On the other hand, an emulsion may be formed and physically stabilized and the lifetime of the droplets in intimate mixture materially increased if a compound, referred to as an emulsifier, is added to the immiscible liquids. Usually only one phase persists in droplet form for a prolonged period of time, and this is referred to as the internal phase which is surrounded by an external phase. An oil-in-water emulsion is one in which the external phase (also called the continuous phase) comprises water or an aqueous solution and the internal phase (also called the discontinuous or disperse phase) comprises an oil or mixture of mutually soluble oils.

Also preferably, the compositions of this invention contain liposomes. Liposomes are vesicular lipid membrane structures enclosing a volume of water. X-ray diffraction studies depict liposomes as being composed of organized lipid bilayers which swell in water to form hydrated multi-lamellar layers that are separated by thin films of water. These bilayers are composed of amphophilic molecules, which possess both hydrophilic and lipophilic properties. The lipid vesicles may be made of phospholipid, single chain nonphospholipid or zwitterionic surfactants. Because of its hydrophobic nature, each bilayer forms a closed membrane with its apolar residues sequestered away from water. Hydrophobic molecules such as retinol will therefore reside in the closed membranes and will not be as likely to be subject to oxidative degradation. Suspensions of liposome vesicles may be described as water-in-oil-in-water (w/o/w) systems. Generally, they are more cosmetically elegant and less greasy than water-in-oil (w/o) emulsions. However, such liposome vesicles need not be formed in order to achieve a low-irritation product. For example, the oil phase of the compositions may contain glyceryl distearate and cholesterol and the like, which are wall-forming surfactants. Other fatty alcohols such as stearyl alcohol may also form a portion of the compositions of this invention.

The retinoids which can be utilized in the products of this invention such that their irritation is reduced upon application to the skin in accordance with the principles of the present invention include retinol (Vitamin A alcohol), retinal (Vitamin A aldehyde), retinyl acetate, retinyl palmitate and mixtures thereof.

DETAILED DESCRIPTION OF THE PREFERRED EMBODIMENTS

As described above, the composition of the invention is in the form of a particular type of emulsion. Most commercial skin care compositions such as the ones containing retinoic acid are oil-in-water emulsion systems. However, in the known commercial systems, certain retinoid compounds, in particular retinol, retinal, retinoic acid, and the retinyl esters, tend to cause substantial irritation to the skin.

The compositions of this invention overcome this difficulty and, instead, provide a composition containing at least one retinoid compound wherein the irritation caused by the retinoid is significantly reduced. The compositions of this invention may be in the form of an emulsion or may contain liposome vesicles.

As used herein, the generally accepted concept of an emulsion applies i.e., an intimate mixture of two immiscible liquids which remains unseparated for an acceptable shelf life (is physically stable) at or about room temperature. Ordinarily, when two immiscible liquids are mechanically agitated, both phases initially tend to form droplets. Thereafter, when the agitation ceases, the droplets quickly coalesce, and the two liquid tends to separate. On the other hand, an emulsion may be formed and physically stabilized and the lifetime of the droplets in intimate mixture materially increased if a compound, referred to as an emulsifier, is added to the immiscible liquids. Usually only one phase persists in droplet form for a prolonged period of time, and this is referred to as the internal phase which is surrounded by an external phase. An oil-in-water emulsion is one in which the external phase (also called the continuous phase comprises water and the internal phase (also called the discontinuous or disperse phase) comprise an oil. A water-in-oil emulsion is one in which the external phase comprises an oil and the internal phase comprises water.

Liposomes are spherical, self-closed structures composed of curved lipid bilayers which entrap part of the solvent, in which they freely float, into their interior. They may consist of one or several concentric membranes. Liposomes are made predominantly fro amphiphiles, a special class of surface active molecules, which are characterized by having a hydrophilic and a hydrophobic group on the same molecule. These molecules are not soluble in water; and, rather than forming solutions, they form colloidal dispersions. Paucilamellar lipid vesicles, of the type described in U.S. Pat. Nos. 4,911,928 and 5,147,723, which are hereby incorporated herein by reference, can be utilized in the compositions of this invention.

It is also preferable to have at least one oil-soluble antioxidant in the compositions of this invention. The oil-soluble antioxidants which are useful in the compositions of the present invention include butylated hydroxytoluene (BHT), ascorbyl palmitate, butylated hydroxyanisole (BHA), a-tocopherol, phenyl-a-naphthylamine, hydroquinone, propyl gallate, nordihydroguiaretic acid, and mixtures thereof as well as any other known oil-soluble antioxidant compatible with the other components of the compositions.

The oil-soluble antioxidants useful in the compositions of this invention should be utilized in a stabilizing effective amount and may range in total from about 0.001 to about 5% based on the weight of the total composition, preferably from about 0.01 to about 1%. The amount of antioxidants utilized in the compositions of the present invention is dependent in part on the specific antioxidants selected, the amount of and specific retinoid being protected and the processing conditions. For example, a retinol formulation should include BHT in the amount of from about 0.01% to about 1% by weight. A retinal formulation should include BHT in the amount of from about 0.01% to about 1% by weight.

The compositions of this invention may also include a chelating agent to minimize metal ion contamination. The retinoid compounds of this invention are sensitive to metal ions and in particular to bi- and tri-valent cations and in certain instances, appear to degrade rapidly in their presence. The chelating agent forms a complex with the metal ions thereby inactivating them and preventing them from affecting the retinoid compounds. Chelating agents which are useful in the compositions of this invention include ethylenediamine tetraacetic acid (EDTA) and derivatives and salts thereof, dihydroxyethyl glycine, citric acid, tartaric acid, and mixtures thereof. The chelating agents should be utlizied in a stabilizing effective amount and may range from about 0.01 to about 2% based on the weight of the total composition, preferably from about 0.05 to about 1%.

The retinoid compounds which are useful in the compositions of the present invention consist of Vitamin A alcohol (retinol), Vitamin A aldehyde (retinal) and Vitamin A esters (retinyl acetate and retinyl palmitate). These retinoids are utilized in the compositions of the present invention in a therapeutically effective amount that may range from about 0.001 to about 5% by weight of the total compositions, preferably from about 0.001 to about 1%.

The skin care compositions of the present invention comprising a water-in-oil emulsion can be in the format of cream or lotion formulations, as desired, by varying the relative quantities of the oil and water phases of the emulsion. The pH of the compositions should be in the range of from about 4 to about 9, and preferably from about 4 to about 7. Most preferably, the pH of the compositions should be at least 5.

Mineral oils, animal oils, vegetable oils and silicones have all been used in cosmetic creams and lotions of the emulsion type. In addition to such oils, other emollients and surface active agents have been incorporated in the emulsions, including glyceryl trioleate, acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, diglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST99), polyethylene glycol 400 distearate and glyceryl stearate; alcohols, such as cetyl alcohol and lanolin alcohol; myristates, such as isopropyl myristate; cetyl palmitate; cholesterol; stearic acid; propylene glycol; glycerine, sorbitol and the like. Thickeners such as natural gums and synthetic polymers, as well as preservatives such as methylparaben, butyl paraben, propylparaben and phenoxyethanol, coloring agents and fragrances also are commonly included in such compositions. Other active ingredients such as sunscreen materials and antimicrobial materials may be utilized in the compositions of the present invention provided that they are physically and chemically compatible with the other components of the compositions.

The essence of the present invention is not within the specific composition per se of the cream or lotion formulation, and any of the many formulations or compositions of the cream or lotion type currently utilized in skin care preparations can be employed provided that it is in a water-in-oil emulsion and is chemically compatible with the retinoid compounds. The ratio of the oil phase of the emulsion to the water phase can be from about 5:95 to about 40:60. The actual ratio of the two phases will depend on the desired final product.

The skin care compositions of the present invention comprising an oil-in-water emulsion can be in the format of cream or lotion formulations, as desired, by varying the relative quantities of the oil and water phases of the emulsion. The pH of the compositions should be in the range of from about 4 to about 10; preferably they should be from about 6 to about 8. It has been found that, in compositions having a pH of about 6 or more, the retinoid is more stable than at pH of less than 6.

Preferably, glycerin is included in the formulations of this invention as a humectant, however, it should be present in relatively low amounts. Preferably, the amount of glycerin should be less than 10% of the total composition. More preferably, it should be less than 5% of the total composition by weight. It is theorized that glycerin may enhance penetration of an active or irritating ingredient, thus increasing the amount of its irritation-producing effects. Thus, glycerin should be present in the composition in a penetration-enhancing effective amount.

Preferably, the inclusion of irritating compounds should be avoided. For example, butylene glycol is potentially irritating and may cause additional irritation in the type of formulations of this invention. Other potentially irritating compounds include soaps, amine-based compounds, surfactants, certain sunscreen active ingredients and compounds which cause the pH of the composition to become either extremely acidic or extremely basic.

A branched-chain fatty alcohol ester such as octyl hydroxy stearate may also contribute to the mildness of the compositions of this invention. Other branched-chain fatty esters may be useful in mitigating the irritating effects of the compositions of this invention.

The advantages of the invention and specific embodiments of the skin care compositions prepared in accordance with the present invention are illustrated by the following examples. It will be understood, however, that the invention is not confined to the specific limitations set forth in the individual examples, but rather to the scope of the appended claims.

EXAMPLE 1

The following formula was made in accordance with the teachings of this invention. The oil phase and water phase were formed separately. The following oil phase ingredients (glyceryl distearate, cholesterol NF, POE 10 stearyl alcohol, ceteareth 20 and stearyl alcohol, ceteareth 20 and cetearyl alcohol, stearyl alcohol) were blended together in a kettle and heated to 80° C. with agitation. Once all the ingredients were melted, the temperature was held at 80° C. for between about five to ten minutes, i.e., until all ingredients were mixed uniformly. Cooling to 65° C. was begun. When the temperature reached 70° C., BHT was added. When the temperature reached 65° C., the following ingredients were added: octyl hydroxystearate, cetyl acetate and acetylated lanolin, $C_{12-15}$ alkyl lactate, and polysorbate 80. Argon diffusion was begun and, subsequently, retinol added to the composition. The temperature was held at 65° C. until the water phase was prepared and ready for addition.

The water phase was prepared as follows: deionized water was added to a kettle and the kettle slowly heated to 80° C. During the heating process, citric acid, sodium citrate and glycerin were added to the water. At 80° C., methylparaben and propylparaben were added. The mixture was held at 80° C. for about five to ten minutes, i.e., until a uniform mixture was obtained. The two phases were then mixed together at 60° C. in accordance with the procedure set forth in U.S. Pat. No. 4,911,928 (Wallach) for making liposomes. The remaining ingredients were added after combination of the two phases and the mixture homogenized using a rotor-stator homogenizer.

| CHEMICAL NAME | % W/W |
| --- | --- |
| Water Phase | |
| Deionized water | 62.490 |
| Glycerin | 4.000 |
| Citric Acid | 0.130 |
| Sodium Citrate | 4.750 |
| Sodium Chloride | 0.100 |
| Methylparaben | 0.200 |
| Propylparaben | 0.030 |
| Oil Phase | |
| Glyceryl Distearate[1] | 2.800 |
| Cholesterol, NF | 1.000 |
| Stearyl Alcohol | 0.500 |

| CHEMICAL NAME | % W/W |
| --- | --- |
| POE10 Stearyl Alcohol[2] | 1.400 |
| Polysorbate 80[3] | 0.700 |
| Ceteareth 20 & Stearyl Alcohol[4] | 3.000 |
| Ceteareth 20 & Cetearyl Alcohol[5] | 3.000 |
| Octyl Hydroxystearate[7] | 6.190 |
| Cetyl Acetate & Acetylated Lanolin[8] | 1.000 |
| $C_{12-15}$ Alkyl Lactate[9] | 1.500 |
| Single Additions | |
| Vitamin A 40 in Polysorbate 20[6] | 0.210 |
| Silicone Emulsion TBM 35060 | 4.000 |
| Polyacrylamide, $C_{13-14}$ Isoparaffin and Laureth-7[10] | 3.000 |

[1]Kessco GDS
[2]Brij 76
[3]Tween 80
[4]Procol ST 20G, an emulsifier
[5]Procol CS 20D, an emulsifier
[6]Retinol in polysorbate 20 40% w/w
[7]Wickenol 171
[8]Acetulan
[9]Ceraphyl 41
[10]TBM 35060, a silicon emulsion
[11]Sepigel 305, a thickener The composition of Example 1 was tested in a modified RIPT (Draize) test as set forth in U.S. patent application Ser. No. 08/415,975. The composition was applied repeatedly to the skin of volunteers. It resulted in extremely low irritation in terms of redness and swelling of the skin (Score=11.5).

EXAMPLE 2

Comparative

A composition of the following formula was made in accordance with the procedure set forth in Example 1.

| CHEMICAL NAME | % W/W |
| --- | --- |
| Water Phase | |
| Deionized water | 58.898 |
| Glycerin | 9.500 |
| Butylene Glycol | 9.500 |
| Citric Acid | 0.120 |
| Sodium Citrate | 4.530 |
| EDTA Disodium | 0.100 |
| Methylparaben | 0.200 |
| Oil Phase | |
| Glyceryl Monostearate | 0.787 |
| Glyceryl Distearate[2] | 1.575 |
| Cholesterol, NF | 1.977 |
| POE10 Stearyl Alcohol[3] | 1.240 |
| Stearyl Alcohol | 1.422 |
| Polysorbate 80[8] | 0.500 |
| Caprylic/Capric Triglyceride[1] | 4.256 |
| Vitamin A 40% w/w in polysorbate 20 | 0.165 |
| BHT | 0.100 |
| Vitamin E Acetate | 0.100 |
| Propylparaben | 0.030 |
| Single Additions | |
| Cyclomethicone | 2.000 |
| Polyacrylamide, $C_{13-14}$ Isoparaffin and Laureth-7 | 3.000 |

[1]Miglyol 812

This formulation has a retinol concentration of about 0.075% W/W and has a high irritation score as measured by the RIPT test (score=377).

EXAMPLES 3

The following composition was made in accordance with the procedure set forth in copending U.S. patent application Ser. No. 08/415,975 and contains 0.04% Retinol. The composition was made such that non-phospholipid liposomes comprising paucilamellar vescicles were created.

| CHEMICAL NAME | % W/W |
| --- | --- |
| Deionized water | 62.490 |
| Glycerin | 4.000 |
| Citric Acid | 0.130 |
| Sodium Citrate | 4.750 |
| Sodium Chloride | 0.100 |
| Methylparaben | 0.200 |
| Octylhydroxystearate[1] | 6.288 |
| Glyceryl Distearate[2] | 2.800 |
| Cholesterol, NF | 1.000 |
| POE10 Stearyl Alcohol[3] | 1.400 |
| Ceteareth 20 and Stearyl Alcohol[4] | 3.000 |
| Ceteareth 20 and Cetearyl Alcohol[5] | 3.000 |
| Stearyl Alcohol | 0.500 |
| Cetyl Acetate and Acetylated Lanolin[6] | 1.000 |
| $C_{12-15}$ Alkyl Lactate[7] | 1.500 |
| Polysorbate 80[8] | 0.700 |
| Propylparaben | 0.030 |
| Vitamin A/Polysorbate 20[9] | 0.112 |
| Silicon Emulsion[a] | 4.000 |
| Polyacrylamide, $C_{13-14}$ Isoparaffin and Laureth-7[11] | 3.000 |

Note:
[1]Wickenol 171, a skin conditioner
[2]Kessco GDS, an emulsifier
[3]Brij 76, an emulsifier
[4]Procol ST 20G, an emulsifier
[5]Procol CS 20D, an emulsifier
[6]Acetulan, a skin conditioner
[7]Ceraphyl 41, an emulsifier
[8]Tween 80, an emulsifier
[9]Retinol 50P, a 50% w/w retinol solution in Polysorbate 20.
[10]TBM 35060, a silicon emulsion
[11]Sepigel 305, a thickener
[a]TBM 35060

This formulation resulted in low irritation when placed on the skin with excellent tolerance when used daily for a four-month period when compared with other retinol containing products under the same test conditions.

EXAMPLE 4

The following formulation was made in accordance with the process set forth in Example 1.

| CHEMICAL NAME | % W/W |
| --- | --- |
| Water Phase | |
| Deionized Water | 62.490 |
| Octyl Hydroxy Stearate | 5.628 |
| Cholesterol | 1.000 |
| POE 10 Stearyl Alcohol | 1.400 |
| Ceteareth 20 and Stearyl Alcohol | 3.000 |
| Ceteareth 20 and Cetearyl Alcohol | 3.000 |
| Stearyl Alcohol | 0.500 |
| Cetyl Acetate and Acetylated Lanolin | 1.000 |
| C12–15 Alkyl Lactate | 1.500 |
| Retinol 40% w/w in Polysorbate 20 | 0.772 |
| Citric Acid | 0.130 |
| Sodium Citrate | 4.750 |
| Sodium Chloride | 0.100 |
| Glycerin | 4.000 |

| CHEMICAL NAME | % W/W |
|---|---|
| Polysorbate 80 | 0.700 |
| Methyl Paraben | 0.200 |
| Propyl Paraben | 0.030 |
| Silicon Emulsion (TBM 35060) | 4.000 |
| Polyacrylamide, C13–14 Isoparaffin and Laureth-7 | 3.000 |

This composition had an irritation score equivalent to that of a comparative formula containing only one-half the amount of retinol in a water-in-oil emulsion containing purified water (49.484%), glycerin (10%), PEG 150 (1%), butylene glycol (4%), trisodium EDTA (0.10%), ascorbic acid (0.10%), sodium citrate (0.10%), pentaerythritol tetraoctanoate (5%), squalene (15%) macademia nut oil (7%), petrolatum (3%), polyglyceryl-2-diisostearate (2%), quaternium 18 hectorite (2.7%), butylparaben (0.10%), ethylparaben (0.10%), BHT (0.05%), tocopheryl acetate (0.10%) and retinol (0.166%).

EXAMPLE 5

The following formulation was made in accordance with the procedure set forth in Example 1.

| CHEMICAL NAME | % W/W |
|---|---|
| Deionized Water | 62.490 |
| Glycerin | 4.000 |
| Citric Acid | 0.130 |
| Sodium Citrate | 4.750 |
| Sodium Chloride | 0.100 |
| Polysorbate 80 | 0.200 |
| Methyl Paraben | 0.200 |
| Propyl Paraben | 0.030 |
| Octyl Hydroxy Stearate | 5.980 |
| Glyceryl Distearate | 2.800 |
| Cholesterol | 1.000 |
| POE 10 Stearyl Alcohol | 1.400 |
| Ceteareth 20 and Stearyl Alcohol | 3.000 |
| Ceteareth 20 and Cetearyl Alcohol | 3.000 |
| Stearyl Alcohol | 0.500 |
| Cetyl Acetate and Acetylated Lanolin | 1.000 |
| Retinol 50% w/w | 0.420 |
| $C_{12-15}$ Alkyl Lactate | 1.500 |
| Silicone Emulsion TBM 35060 | 4.000 |
| Polyacrylamide, C13–14 Isoparaffin and Laureth-7 | 3.000 |

This formulation resulted in very low irritation on human skin.

EXAMPLE 6

The following formulation was made in accordance with the procedure set forth in Example 1 and differs from Example 5 in that $C_{12-15}$ Alkyl Lactate was omitted from the formulation.

| | |
|---|---|
| Deionized Water | 62.490 |
| Glycerin | 4.000 |
| Citric Acid | 0.130 |
| Sodium Citrate | 4.750 |
| Sodium Chloride | 0.100 |
| Polysorbate 80 | 0.700 |
| Methyl Paraben | 0.200 |
| Propyl Paraben | 0.030 |
| Octyl Hydroxy Stearate | 7.510 |
| Glyceryl Distearate | 2.800 |
| Cholesterol | 1.000 |
| POE 10 Stearyl Alcohol | 1.400 |
| Ceteareth 20 and Stearyl Alcohol | 3.000 |
| Ceteareth 20 and Cetearyl Alcohol | 3.000 |
| Stearyl Alcohol | 0.500 |
| Cetyl Acetate and Acetylated Lanolin | 1.000 |
| Retinol 40% w/w | 0.390 |
| Silicone Emulsion TBM 35060 | 4.000 |
| Polyacrylamide, C13–14 Isoparaffin and Laureth-7 | 3.000 |

This formulation resulted in very low irritation on human skin similar to that of the formulation of Example 5.

EXAMPLE 7

The following formulation was made in accordance with the procedure set forth in Example 1. It has a lower buffer salt concentration than the formulation set forth in Example 5.

| | |
|---|---|
| Deionized Water | 67.240 |
| Glycerin | 4.000 |
| Citric Acid | 0.130 |
| Sodium Chloride | 0.100 |
| Polysorbate 80 | 0.700 |
| Methyl Paraben | 0.200 |
| Propyl Paraben | 0.030 |
| Octyl Hydroxy Stearate | 6.010 |
| Glyceryl Distearate | 2.800 |
| Cholesterol | 1.000 |
| POE 10 Stearyl Alcohol | 1.400 |
| Ceteareth 20 and Stearyl Alcohol | 3.000 |
| Ceteareth 20 and Cetearyl Alcohol | 3.000 |
| Stearyl Alcohol | 0.500 |
| C12–C15 Alkyl Lactate | 5.000 |
| Cetyl Acetate and Acetylated Lanolin | 1.000 |
| Retinol 40% w/w | 0.390 |
| C12–15 Alkyl Lactate | 1.500 |
| Silicone Emulsion TBM 35060 | 4.000 |
| Polyacrylamide, C13–14 Isoparaffin and Laureth-7 | 3.000 |

This formulation contains approximately 0.15% retinol. This formulation resulted in higher irritation on human skin than that of the other examples.

EXAMPLE 8

The following formulation was made in accordance with the procedure set forth in Example 1, which differs from Example 5 in that the sodium citrate buffer is substituted with dibasic sodium phosphate.

| | |
|---|---|
| Deionized Water | 65.240 |
| Glycerin | 4.000 |
| Citric Acid | 0.130 |
| Dibasic Sodium Phosphate | 0.500 |
| Sodium Chloride | 0.100 |
| Polysorbate 80 | 0.700 |
| Methyl Paraben | 0.200 |
| Propyl Paraben | 0.030 |
| Octyl Hydroxy Stearate | 2.510 |
| Glyceryl Distearate | 2.800 |
| Cholesterol | 1.000 |
| POE 10 Stearyl Alcohol | 1.400 |

| | |
|---|---|
| Ceteareth 20 and Stearyl Alcohol | 3.000 |
| Ceteareth 20 and Cetearyl Alcohol | 3.000 |
| Stearyl Alcohol | 0.500 |
| Cetyl Acetate and Acetylated Lanolin | 1.000 |
| Retinol 40% w/w | 0.390 |
| Retinol 50% W/W | 0.390 |
| Silicone Emulsion TBM 35060 | 4.000 |
| Polyacrylamide, $C_{13-14}$ Isoparaffin and Laureth-7 | 3.000 |

This formulation resulted in relatively high irritation on human skin, similar to that of Example 4 (comparison formulation) and Example 7.

EXAMPLES 9A AND 9B

The following formulations have the same chemical composition, however 9A was processed in accordance with the procedure set forth in Example 1, which results in paucilamellar vesicles, whereas formulation 9B was processed using only the rotor-stator homogenizer after blending of the oil and water phases.

| CHEMICAL NAME | % W/W |
|---|---|
| Deionized water | 62.490 |
| Glyceryl Distearate | 2.800 |
| Octyl Hydroxystearate | 5.980 |
| Cholesterol, NF | 1.000 |
| Citric Acid | 0.130 |
| Sodium Citrate | 4.750 |
| Ceteareth 20 & Stearyl Alcohol | 3.000 |
| Ceteareth 20 & Cetearyl Alcohol | 3.000 |
| POE10 Stearyl Alcohol | 1.400 |
| Cetyl Acetate & Acetylated Lanolin | 1.000 |
| Stearyl Alcohol | 0.500 |
| Silicone Emulsion TBM 35060 | 4.000 |
| Glycerin | 4.000 |
| Methylparaben | 0.200 |
| Propylparaben | 0.030 |
| Sodium Chloride | 0.100 |
| Polysorbate 80 | 0.700 |
| $C_{12-15}$ Alkyl Lactate | 1.500 |
| Retinol 40% W/W | 0.420 |
| Polyacrylamide, $C_{13-14}$ Isoparaffin and Laureth-7 | 3.000 |

The irritation ratings for the use of both of these compositions were very low.

Thus, substantially non-irritating compositions containing retinoid compounds may be made using the compositions of this invention.

EXAMPLE 10

The following formulation was made in accordance with the procedure set forth in Example 1.

| CHEMICAL NAME | % W/W |
|---|---|
| Octyl hydroxystearate | 6.2942 |
| Glyceryl distearate | 2.8000 |
| Cholesterol | 1.0000 |
| POE 10 Stearyl alcohol | 1.4000 |
| Ceteareth 20 & Stearyl alcohol | 3.0000 |
| Ceteareth 20 & Cetearyl alcohol | 3.0000 |
| Stearyl alcohol | 0.5000 |
| Cetyl acetate & acetylated lanolin | 1.0000 |
| C12–15 Alcohols lactate | 1.5000 |
| Retinol (50% w/w in Polysorbate 20) | 0.1058 |
| BHT | 0.1000 |
| Citric acid anhdyrous | 0.1500 |
| Trisodium citrate dihydrate | 0.8500 |
| Ascorbic acid | 0.0100 |
| Glycerin | 4.0000 |
| Polysorbate 80 | 0.7000 |
| Disodium EDTA | 0.2000 |
| Phenoxyethanol | 0.7300 |
| Methyl paraben | 0.2500 |
| Propyl paraben | 0.1500 |
| Dimethicone, 100 cst | 2.5000 |
| Polyacrylamide, C13–14 Isoparaffin and Laureth-7 | 0.5000 |
| Fragrance | 0.0500 |
| Water | 69.2100 |

This formulation had a pH of about 5.6 and resulted in very low irritation on human skin.

EXAMPLE 11

The following formulation was made in accordance with the procedure set forth in Example 1.

| CHEMICAL NAME | % W/W |
|---|---|
| Octyl hydroxystearate | 6.1355 |
| Glyceryl distearate | 2.8000 |
| Cholesterol | 1.0000 |
| POE 10 Stearyl alcohol | 1.4000 |
| Ceteareth 20 & Stearyl alcohol | 3.0000 |
| Ceteareth 20 & Cetearyl alcohol | 3.0000 |
| Stearyl alcohol | 0.5000 |
| Cetyl acetate & acetylated lanolin | 1.0000 |
| C12-15 Alcohols lactate | 1.5000 |
| Retinol (50% w/w in Polysorbate 20) | 0.2645 |
| BHT | 0.1000 |
| Citric acid anhydrous | 0.0300 |
| Trisodium citrate dihydrate | 1.0330 |
| Ascorbic acid | 0.0100 |
| Glycerin | 4.0000 |
| Polysorbate 80 | 0.7000 |
| Disodium EDTA | 0.2000 |
| Phenoxyethanol | 0.7300 |
| Methyl paraben | 0.2500 |
| Propyl paraben | 0.1500 |
| Dimethicone, 100 cst | 2.5000 |
| Polyacrylamide, C13–14 Isoparaffin and Laureth-7 | 0.5000 |
| Fragrance | 0.0500 |
| Water | 69.1970 |

This formulation had a pH of about 6.2 and resulted in very low irritation on human skin.

What is claimed is:

1. A cosmetic composition comprising:

| | |
|---|---|
| octyl hydroxysterate | 6.1355% w/w, |
| glyceryl disterate | 2.8000% w/w, |
| cholesterol | 1.0000% w/w |
| POE 10 stearyl alcohol | 1.4000% w/w, |
| Ceteareth 20 & stearyl alcohol | 3.0000% w/w, |
| Ceteareth 20 & cetearyl alcohol | 3.0000% w/w, |
| Stearyl alcohol | 0.5000% w/w, |
| Cetyl acetate & acetylated lanolin | 1.0000% w/w, |
| C12–C15 alcohols lactate | 1.5000% w/w, |

-continued

| | |
|---|---|
| Retinol (50% w/w in polysorbate 20) | 0.2645% w/w, |
| BHT | 0.1000% w/w, |
| Citric acid anhydrous | 0.0300% w/w, |
| trisodium citrate dihydrate | 1.0330% w/w, |
| ascorbic acid | 0.0100% w/w, |
| glycerin | 4.0000% w/w, |
| polysorbate 80 | 0.7000% w/w, |
| disodium EDTA | 0.2000% w/w, |
| phenoxyethanol | 0.7300% w/w, |
| methyl paraben | 0.2500% w/w, |
| propyl paraben | 0.1500% w/w, |

-continued

| | |
|---|---|
| dimethicone, 100 cst | 2.5000% w/w, |
| polyacrylamide, C13–C14 | 0.0500% w/w, |
| isoparaffin & laureth-7 | 0.5000% w/w, |
| fragrance | |
| and | |
| water | 69.1970% w/w. |

* * * * *